(12) United States Patent
Levine et al.

(10) Patent No.: US 11,504,508 B2
(45) Date of Patent: Nov. 22, 2022

(54) EXTENDED-TIP ANGIOPLASTY DEVICE AND METHOD

(71) Applicants: Jonathan Levine, Clarendon Hills, IL (US); Timothy Murphy, Providence, RI (US)

(72) Inventors: Jonathan Levine, Clarendon Hills, IL (US); Timothy Murphy, Providence, RI (US)

( * ) Notice: Subject to any disclaimer, the term of this patent is extended or adjusted under 35 U.S.C. 154(b) by 254 days.

(21) Appl. No.: 16/360,834

(22) Filed: Mar. 21, 2019

(65) Prior Publication Data
US 2020/0297980 A1 Sep. 24, 2020

(51) Int. Cl.
*A61M 25/10* (2013.01)
*A61M 25/00* (2006.01)
(Continued)

(52) U.S. Cl.
CPC ........... *A61M 25/104* (2013.01); *A61B 6/481* (2013.01); *A61B 6/504* (2013.01);
(Continued)

(58) Field of Classification Search
CPC ............ A61M 25/104; A61M 25/0026; A61M 25/0068; A61M 2025/1061; A61M 25/09;
(Continued)

(56) References Cited

U.S. PATENT DOCUMENTS 3,382,872 A 5/1968 Rubin
4,641,654 A 2/1987 Samson
(Continued)

OTHER PUBLICATIONS

Development of angioplasty spawned 40 years of innovation, exploration. Cardiology Today, Dec. 2017, https://www.heallo.com/news/cardiology/20171205/development-of-angioplasty-spawned-40-years-of-innovation-exploration.
(Continued)

*Primary Examiner* — Kami A Bosworth
*Assistant Examiner* — Avery Smale

(57) ABSTRACT

Disclosed is an angioplasty balloon catheter and method of use, said angioplasty balloon catheter includes an elongated tip end with physical characteristics nearly identical to a standard angiographic diagnostic catheter. The elongated tip end extends approximately between 2 cm to 75 cm beyond a distal end of a balloon, depending upon embodiments. The tip of the elongated tip end may be angled or straight depending upon embodiments and may or may not have a plurality of side holes in addition to an end hole depending on embodiments. The elongated tip end permits the angioplasty balloon catheter to tract more easily across tortuous or markedly angulated segments of a dialysis graft or fistula, minimizing complications that can result with currently available devices. If angulated, the elongated tip end also enables a user to selectively catheterize an artery without needing a separate diagnostic catheter to do so, and enable tracking and cornering across sharply angulated vessel segments. Whether with an angled or straight distal catheter portion, the angioplasty balloon catheter disclosed herein allows the user to perform angioplasty of an inflow segment of a dialysis graft or fistula and then perform post angioplasty angiographic imaging without the need to exchange the angioplasty balloon catheter for a diagnostic catheter, advance the balloon catheter into the native artery, or perform a blowback angiographic run, thereby improving safety and reducing procedure time.

16 Claims, 10 Drawing Sheets

(51) Int. Cl.
*A61B 6/00* (2006.01)
*A61M 25/09* (2006.01)
*A61B 17/3207* (2006.01)

(52) U.S. Cl.
CPC . *A61B 17/320725* (2013.01); *A61M 25/0026* (2013.01); *A61M 25/0068* (2013.01); *A61M 25/0097* (2013.01); *A61M 25/09* (2013.01); *A61M 2025/1061* (2013.01)

(58) Field of Classification Search
CPC .............. A61M 25/0097; A61M 25/10; A61M 2025/1052; A61M 2025/1093; A61M 2025/1043; A61M 25/007; A61B 6/504; A61B 17/320725; A61B 6/481
See application file for complete search history.

(56) References Cited

U.S. PATENT DOCUMENTS

| | | | | |
|---|---|---|---|---|
| 4,777,951 | A * | 10/1988 | Cribier | A61M 25/0023 600/485 |
| 4,842,590 | A | 6/1989 | Tanabe | |
| 5,087,247 | A | 2/1992 | Horn | |
| 5,328,469 | A | 7/1994 | Coletti | |
| 5,538,510 | A | 7/1996 | Fontirroche | |
| 6,322,577 | B1 | 11/2001 | McInnes | |
| 6,402,720 | B1 | 6/2002 | Miller | |
| 7,873,404 | B1 * | 1/2011 | Patton | A61B 6/504 600/433 |
| 8,532,749 | B1 | 9/2013 | Patton | |
| 9,056,190 | B2 | 6/2015 | Simpson | |
| 9,205,223 | B2 | 12/2015 | Wilson | |
| 9,216,274 | B2 | 12/2015 | Arana | |
| 10,149,960 | B2 | 12/2018 | Franklin | |
| 2001/0035456 | A1 * | 11/2001 | Lennox | G06Q 20/26 235/379 |
| 2002/0042593 | A1 * | 4/2002 | Mickley | A61M 29/02 604/102.01 |
| 2002/0052576 | A1 * | 5/2002 | Massengale | A61M 25/0074 604/164.01 |
| 2005/0209559 | A1 | 9/2005 | Thornton | |
| 2006/0173298 | A1 * | 8/2006 | Tucker | A61B 5/287 600/433 |
| 2008/0249465 | A1 | 10/2008 | Ryder | |
| 2009/0204134 | A1 * | 8/2009 | Kassab | A61B 5/1076 606/159 |
| 2011/0125132 | A1 * | 5/2011 | Krolik | A61M 25/1002 604/509 |
| 2011/0282369 | A1 * | 11/2011 | Krolik | A61B 17/320725 606/198 |
| 2012/0271339 | A1 * | 10/2012 | O'Beirne | A61M 25/104 606/194 |
| 2014/0135789 | A1 * | 5/2014 | Shireman | A61N 1/056 606/129 |
| 2014/0316263 | A1 | 10/2014 | Murphy | |
| 2018/0008801 | A1 * | 1/2018 | Solar | A61M 25/0068 |

OTHER PUBLICATIONS

Beegum Zabina, et al. Morphological and morphometric study of coronary sinus in North Indian Population. Journal of Clinical and Diagnostic Research. Sep. 2017, vol. 11(9): AC15-AC19.

Lalit Mehra, et al. Anatomical consideration and potential complications of coronary sinus catheterisation. Journal of Clinical and Diagnostic Research. Feb. 2016, vol. 10(2): AC12-AC15.

J. P. De Vries, et al. First- and second-generation drug-eluting balloons for femoro-popliteal arterial obstructions: update of technique and results. J Cardiovasc Surg (Torino). Jun. 2013;54(3):327-32.

S. Zia, et al. Safety and Feasibility of Transradial Access for Noncoronary and Peripheral Vascular Interventions. Ann Vasc Surg. Nov. 2018;53:255-261.

* cited by examiner

EXTENDED-TIP ANGIOPLASTY DEVICE AND METHOD

FIELD OF THE INVENTION

The present invention relates to medical devices and vascular interventions. More particularly, the present invention is directed to devices used for the diagnosis and angioplasty of intravascular stenoses.

CROSS-REFERENCE TO RELATED APPLICATIONS

This application claims priority under 35 U.S.C. § 119 and 35 U.S.C. § 120 of provisional patent application No. 62/703,873, EFS ID 33298956, confirmation number 9403, filed Jul. 26, 2018, entitled "Angioplasty Balloon Catheters Having an Elongated Leading End", by inventor Jonathan Alan Levine, the entirety of which is incorporated herein by reference.

BACKGROUND

U.S. Patents

| Pat. No. | Issue Date | Patentee |
| --- | --- | --- |
| U.S. Pat. No. 4641654 | Feb. 10, 1987 | Wilfred J. Samson |
| U.S. Pat. No. 4842590 | Jun. 27, 1989 | Susumu Tanabe |
| U.S. Pat. No. 5087247 | Feb. 11, 1992 | Josephe B. Horn |
| U.S. Pat. No. 5328469 | Jul. 12, 1994 | Roger Coletti |
| U.S. Pat. No. 5538510 | Jul. 23, 1996 | Carlos A. Fontirroche |
| U.S. Pat. No. 6322577 | Nov. 27, 2001 | Peter R. McInnes |
| U.S. Pat. No. 6402720 | Jun. 11, 2002 | Jay Frederic Miller |
| U.S. Pat. No. 7873404 | Jan. 18, 2011 | Chris Patton |
| U.S. Pat. No. 8532749 | Sep. 10, 2013 | Chris Patton |
| U.S. Pat. No. 10149962 | Dec. 11, 2018 | Curtis J. Franklin |
| U.S. Pat. No. 3382872 | May 14, 1968 | Melvin L. Rubin |

U.S. Patent Applications

U.S. patent application Ser. No. 13/868,354, publication date Oct. 23, 2014, Inventor: Timothy Murphy Nonpatent Literature K. Steiner. Pathophysiology of Stenosis Within AV Fistulas and Mechanisms of angioplasty. Endovascular Today 2016; 15(6): 28-32.

I Bountouris, G Kritikou, N. Degermetzoglou, K. I. Avgerinos. A Review of Percutaneous Transluminal Angioplasty in Hemodialysis Fistula. International Journal of Vascular Medicine 2018; Article ID 1420136, pp. 1-5.

A. Asif, O. Lenz, D. Merrill, et al. Percutaneous management of perianastomotic stenosis in arteriovenous fistulae: results of a prospective study. Kidney Int. 2006; 69:1904-1909.

M. Napoli, R. Prudenzano, F. Russo, A. L. Antonaci, M. Aprile, and E. Buongiorno, "Juxta-anastomotic stenosis of native arteriovenous fstulas: surgical treatment versus percutaneous transluminal angioplasty.," The Journal of Vascular Access, vol. 11, no. 4, pp. 346-351, 2010.

B. Long, N. Brichart, P. Lermusiaux et al., "Management of perianastomotic stenosis of direct wrist autogenous radialcephalic arteriovenous accesses for dialysis," Journal of Vascular Surgery, vol. 53, no. 1, pp. 108-114, 2011.

H. Kwon, J. Y. Choi, H. K. Ko et al., "Comparison of surgical and endovascular salvage procedures for juxta-Anastomotic stenosis in autogenous wrist radiocephalic arteriovenous fistula," Annals of Vascular Surgery, vol. 28, no. 8, pp. 1840-1846, 2014.

S. H. Ahn, E. A. Prince, G. J. Dubel. Carotid Artery Stenting: Review of Technique and Update of Recent Literature. Semin Intervent Radiol. 2013 September; 30(3): 288-296.

J. P. De Vries, A. Karimi, B. Fioole, M. Van Leersum, D. A. Werson, D. A. Van Den Heuvel. First- and second-generation drug-eluting balloons for femoro-popliteal arterial obstructions: update of technique and results. J Cardiovasc Surg (Torino). 2013 June; 54(3):327-32.

S. Zia, K. Singh, A. Juneja, J. Schor, J. Deitch.Safety and Feasibility of Transradial Access for Noncoronary and Peripheral Vascular Interventions. Ann Vasc Surg. 2018 November; 53:255-261.

F. Hosam, M. D. El-Sayed. Retrograde Pedal/Tibial Artery Access for Treatment of Infragenicular Arterial Occlusive Disease. Methodist Debakey Cardiovasc J. 2013; 9(2): 73-78.

Historically, when discussing the diagnosis and treatment of stenoses (areas of luminal narrowing) in arteries and veins, there have been two distinct types of catheters used, diagnostic catheters and angioplasty (angioplasty) balloon catheters. Diagnostic catheters are used to selectively catheterize vascular territories and to inject radiopaque contrast into them in order to identify vascular pathology using fluoroscopy or radiography. Diagnostic catheters are made of materials of varying stiffness and lubricity and comprise shaped distal segments in such a way as to allow them to select vessel origins and bifurcations, and to navigate tortuous and angulated vascular anatomy. Angioplasty balloon catheters are used to dilate the areas of vessel narrowing. Percutaneous transluminal balloon angioplasty (angioplasty) is the standard technique for the treatment of the AVAC stenoses. Angioplasty balloon catheters comprise a catheter with a balloon mounted at its distal end. The balloon is inflated during operation to treat the stenotic lesion in question, and then deflated and removed from the body. Although there have been some improvements regarding balloon materials as they apply primarily to such physical characteristics as rated burst pressure and compliance, the basic design of the angioplasty balloon catheter itself has not changed since the first vascular angioplasties were performed in 1974. The typical angioplasty balloon catheter used in the peripheral circulation has an overall length of approximately 75-150 cm, with the length of the balloon approximately 2-20 cm, depending on the length of the lesion being treated.

Hemodialysis access fistulas and grafts are prone to stenoses, and are an area in the body where balloon angioplasty is often performed. When kidney function decreases below 10% to 15%, the kidneys are no longer able to adequately filter the blood and make urine. This causes certain toxins to build up in the bloodstream along with excess fluid. Hemodialysis is a therapy that filters metabolic waste, removes extra fluid and balances electrolytes. In hemodialysis, blood is removed from the body and filtered through a man-made membrane called a dialyzer and then the filtered blood is returned to the body. To perform hemodialysis there needs to be some sort of access created to get the blood from the body to the dialyzer and back to the body. Of the more than 2 million people on dialysis, nearly 500,000 dialyze with either an arterio-venous graft or autologous arterio-venous fistula, the latter of which is preferred by the National Kidney Foundation. Both of these modalities will heretofore be referred to as the AV Access Circuit (AVAC). AVAC's are surgically created vascular circuits that involve a direct connection between the arterial and venous circulations. The AV fistula is accomplished by anastomosing an artery of the upper or lower arm to a corresponding vein without the use of any foreign material. On the other hand, a graft is created by connecting an artery to a vein with the aid of a tubular conduit, usually made of polytetrafluoroethylene, polyester, nylon, polyethylene terephthalate, or other similar material. In an AV graft, stenoses commonly occur at the graft-artery and graft-venous anastomoses. In an autologous arterio-venous fistulae, stenoses tend to occur at the surgical arterio-venous anastomosis as well as what is referred to as the juxta-anastomotic segment, which is the segment of vein that lies within the first 4-5 cm of the outflow vein immediately central to the anastomosis as well as within the native artery just proximal to the anastomosis. These are referred to as inflow lesions of the AVAC. However, stenoses can develop anywhere in the AVAC, secondary to intimal hyperplasia from altered flow dynamics, surgical intervention as well as vessel trauma from cannulation, or catheter insertion, during the dialysis treatment itself. When these intravascular stenoses develop, the velocity of blood flow within the AVAC decreases, which can compromise the quality of the dialysis treatment secondary to reduced clearance of toxins and ultimately lead to complete thrombosis of the AVAC and loss of the access itself. The latter requires surgical creation of an entirely new access for dialysis treatment.

In order to perform angioplasty of AVAC stenoses in accordance with currently accepted practice standards, prior to angioplasty of the AVAC inflow, a diagnostic catheter is advanced into the native artery upstream from the arterial-venous anastomosis. Contrast is injected through the catheter and medical images obtained in order to define the vascular anatomy and delineate any underlying areas of stenosis requiring treatment. Then, usually using a diagnostic catheter, often with a shaped tip to facilitate cannulation of a blood vessel, catheter access beyond the stenosis is obtained. In the case of AVAC's with juxta-anastomotic stenoses, engaging the arterial anastomosis must be done in order to advance the entire catheter system into an upstream artery. Once the stenotic lesion is defined by contrast injection through a diagnostic catheter in the upstream artery, the diagnostic catheter is removed over a guidewire in situ and exchanged for the angioplasty balloon catheter, introduced over the same guidewire. Typically, the angioplasty balloon catheter is advanced through the skin via a vascular sheath placed at the time of initial AVAC access. Alternatively, it may be advanced without the aid of a sheath, so called sheathless or bareback technique. The balloon segment of the traditional angioplasty balloon catheter is then positioned by the operator across the stenotic lesion so that it straddles the area of vessel narrowing. The balloon is then inflated using any of numerous industry standard balloon inflation devices. The inflated angioplasty balloon exerts radial force against the narrowed vessel lumen, with the goal of transforming the diameter of the vessel to a second, larger-diameter state.

After angioplasty is performed, angiographic imaging with the use of fluoroscopy and intravascular contrast is required to document not only the success or failure of the angioplasty, but to evaluate for any potential complications that can occur as a result of the intervention. Without limitations, such complications can include arterial dissection, arteriovenous spasm, thrombus formation, distal embolization of thrombus, arteriovenous rupture with subsequent extravasation of blood, and contrast agent into the surrounding soft tissues. One typical option after angioplasty has been completed is to withdraw the angioplasty balloon catheter over the guidewire and exchange it under direct fluoroscopic visualization for a diagnostic catheter. This diagnostic catheter is advanced across the treated stenotic segment and upstream into the native artery for several centimeters prior to contrast injection. This way, the entire AVAC inflow may be evaluated from a single angiographic acquisition. Alternatively, after angioplasty of the stenosis in question, the angioplasty balloon may be deflated and advanced over the guidewire into the native artery for a distance similar to an angiographic catheter, then the guidewire removed and contrast injected through the guidewire lumen, opacifying the angioplasty site. The final and the least recommended option for evaluation of the treated AVAC inflow is called a "blowback", in which the deflated angioplasty balloon is withdrawn completely across the treated segment closer to the access point, the guidewire is removed, the balloon re-inflated to occlude the outflow just past the treated segment and contrast injected through the angioplasty balloon catheter end hole. The treated segment is subsequently evaluated in a retrograde fashion as contrast refluxes across the AVAC inflow.

All currently available angioplasty balloon catheters suffer from the same disadvantages when used to treat stenoses of hemodialysis AVAC arterial anastomoses:

(a) Distal tips that are stiff and inflexible may cause trauma to a blood vessel when crossing a stenosis, especially if the vessel is angled beyond the stenosis.

(b) Inability to dilate a vessel safely with an acute angle just beyond the stenosis because stiff tips can damage a treated blood vessel beyond a stenosis when an angioplasty balloon is inflated.

(c) Kinking of the guidewire when an angioplasty balloon is inflated in a vessel with an acute angle just beyond the stenosis.

(d) In the case of AVAC angioplasty, retraction of the angioplasty balloon from the site post-angioplasty puts the catheter downstream from the angioplasty site, which is not a useful location from where to perform angiography to assess the result of the angioplasty, requiring complex maneuvers to obtain post-angioplasty image documentation of the results.

(e) Because standard angioplasty balloon catheters don't facilitate diagnostic angiography after AVAC angioplasty, catheter exchanges are often done to obtain post-angioplasty medical images using fluoroscopy or radiography, which increases procedure time.

(f) Because standard angioplasty balloon catheters don't facilitate diagnostic angiography after AVAC angioplasty, catheter exchanges are often done to obtain post-angioplasty medical images using fluoroscopy or radiography, which increases equipment costs.

(g) Because standard angioplasty balloon catheters don't facilitate diagnostic angiography after AVAC angioplasty, catheter exchanges are often done to obtain post-angioplasty medical images using fluoroscopy or radiography, which increases radiation to the patient and operator.

(h) Use of a "blow back" technique after AVAC angioplasty can cause vessel injury or embolization of plaque, intimal debris, or blood clot retrograde into the arterial circulation, causing ischemic complications including pain, ulceration, loss of sensation, and gangrene, and can even result in amputation.

(i) Use of a "blow back" technique after AVAC angioplasty requires loss of guidewire access across the treated lesion, which may make it difficult or impossible to negotiate across again if a problem is discovered during diagnostic angiography, like vessel dissection, occlusion, or rupture.

(j) Because standard angioplasty balloon catheters don't facilitate diagnostic angiography after AVAC angioplasty, the balloon catheter is typically removed and exchanged for a diagnostic catheter, but if a complication is observed during post-angioplasty diagnostic imaging, having to exchange catheters first to perform the diagnostic angiogram and then again to replace the balloon catheter, which is used to tamponade the hemorrhage, could allow substantial hemorrhage into the soft tissues or extravasated out of the patient's body.

(k) Conventional angioplasty catheters are not useful to perform selective catheterization of a blood vessel, and therefore usually are placed only after a diagnostic catheter has been used to selectively catheterize a blood vessel to be treated.

(l) When angioplasty balloon catheters are used without a sheath, multiple catheter exchanges to perform diagnostic angiography and angioplasty can result in hemorrhage into the soft tissues surrounding the vascular access site due to an imperfect profile of the angioplasty balloon, and use of a sheath for AVAC angioplasty requires a larger access hole than without a sheath, which can also increase the risk of hemorrhage.

(m) Conventional blunt-tip angioplasty balloon catheters may occasionally not be able to be advanced across a stenosis, because of the stenosis severity, configuration, or composition.

SUMMARY

Angioplasty balloon catheters currently used in treatment of stenoses in the AVAC are similar to those that have been developed for other vascular territories. The vascular anatomy in the AVAC differs from every other vascular territory found in the typical human body. Because of the surgically created communication between an artery and a vein during creation of the AVAC, it represents the only situation where a wire or catheter can be advanced from the venous side of the circulation to the arterial side without either going extravascular between the two systems or going from the pulmonary to the systemic circulation across the heart valves. These surgically-created connections are often very sharply angulated and tortuous; more so than most native arterial vascular territories. Because of this unique anatomy, when performing angioplasty of the juxta-anastomotic segment of the AVAC, the arterial anastomosis itself, or even the native artery proximal to the anastomosis, the wire and catheter could be used to cannulate several inches to several feet beyond the target lesion. In other words, there is nearly endless running room beyond the target lesion, in contrast to most vascular stenoses outside of the AVAC, particularly those related to the arterial supply of end organs and in lesions of the distal arterial bed of the upper and lower extremity arterial systems.

Another difference between the treatment of inflow stenoses in an AVAC, compared to arterial and venous stenoses in the rest of the body, is the anatomic location where the pre and post angioplasty imaging is performed relative to the point on the vessel accessed for the purpose of intervention. In order to adequately visualize a vascular stenosis using fluoroscopy or radiography the contrast material must be injected upstream from the target lesion. As venous blood flow is centripetal relative to the heart, pre-angioplasty imaging of venous stenoses is performed with a sheath or diagnostic catheter peripheral or distal to the target lesion. Conversely, because arterial blood flow is centrifugal relative to the heart imaging of arterial stenoses is performed with contrast injected central to the target lesion. It is convention that for post angioplasty imaging of the angioplasty site is performed through a sheath only, with wire access maintained across the treated lesion, but there are other permutations of this procedure, such as use of a diagnostic catheter with a larger inner diameter (I.D.) than the outer diameter (O.D.) of the guidewire sufficient so that contrast can be injected around the guidewire if an appropriate hub adapter (e.g., Touhy-Borst) is used, especially if a small O.D. guidewire is used. Maintenance of access across the treated lesion is important so repeat angioplasty or stent placement can be facilitated in the event of vessel occlusion or rupture. If wire access is lost so that post angioplasty imaging may be done with a diagnostic catheter proximal to the lesion, it may not be possible to cross the treated lesion again with the wire, in the event of vessel dissection, rupture or other complication which compromises vessel lumen integrity.

AVAC angioplasties are also often complicated by a more acute angle at the level of the arterio-venous anastomosis, rather than straight or obtuse angles usually observed at angioplasty sites in native arteries, or veins. Acute angles at anastomoses are common with autologous AV fistulae, and more particularly forearm radial-cephalic fistulae. Although it is usually possible to advance a guidewire from the venous limb of the AVAC into the arterial limb, it is often difficult, if not impossible, to get a conventional angioplasty balloon to corner and track over the wire as they are too stiff to conform to such a steep angle. Attempts to do so often cause the wire to kink. Attempts to advance the balloon further at that point can cause severe vessel injury.

Many of the disadvantages of conventional angioplasty balloon catheters can be improved using an extended-tip angioplasty balloon catheter as disclosed herein. An extended-angioplasty balloon catheter is particularly useful as a means to perform angioplasty at a site in which a blood vessel emanates beyond the stenosis at a substantial angle. There are applications for an extended-tip angioplasty balloon catheter in arteries, in veins, and in arteriovenous fistulas or grafts (AVAC's).

Those familiar with the manufacturer of angioplasty balloon catheters will understand that they are medical devices comprising tubes made of plastic, including among others polyester, polyethylene, nylon, polyamide, homopolymers, copolymers and blends of homopolymers and copolymers, usually extruded, usually multilumen tubes, with an expansible balloon securely attached thereon and disposed toward one end of the tube, with at least a first lumen used as a means for slidable passage of a guidewire or injection of fluids there through, and at least a second lumen used as a means for inflation of said angioplasty balloon. Said angioplasty balloon catheters typically include a hub end, or proximal end, usually comprising a plurality of adapters, often one such adapter of which may permit union of the catheter first lumen with other medical devices such as syringes and infusion tubing, and at least a second adapter that is used for injection of pressurized fluids or gas through at least a second lumen to inflate said angioplasty balloon, and a tip end, or distal end, that is the leading end first introduced into a patient, that is the initial end of the angioplasty balloon catheter that enters any vessel or stenosis. Thus, said angioplasty balloon catheter has a proximal segment, extending from the hub end to the distal aspect of the balloon, and a distal segment, extending from said distal aspect of the balloon to the tip end. An alternative configuration of angioplasty balloon catheters is the "rapid exchange" version, which comprises an angioplasty balloon catheter in which only the second lumen extends from the hub end along the entire length of the angioplasty balloon catheter proximal to the balloon. The extended-tip segment of an extended-tip angioplasty balloon catheter beyond the balloon could be composed of the same material as the catheter between the hub and the balloon, but also could be made of a more compliant material, or even a material of variable durometer throughout its length, than the catheter between the hub and the balloon. The distal extended—tip segment could be integral to the angioplasty balloon catheter, or a separate component that is attached to the proximal segment using heat welding, adhesive, or other attachment means. The angioplasty balloon could be uncoated, or coated with antiproliferative medication, for example paclitaxel, tacrolimus, everolimus, and the like, in order to deposit antiproliferative medication at the site of balloon inflation, as a means to improve longevity of the angioplasty result. The angioplasty balloon may be affixed longitudinal with cutting blades, as is known to those familiar with the art. The extended-tip segment may be a similar outer diameter (O.D.) as the catheter between the hub and the balloon, or could be a smaller diameter, or a variable taper, for example, a smaller diameter at its tip with progressive increase in its O.D. moving towards the balloon until it is similar O.D. to the catheter between the hub and the balloon. Another embodiment of an extended-tip angioplasty balloon catheter has a variable diameter in the catheter segment between the hub and the balloon, to compensate for the relatively larger O.D. of the balloon compared to the catheter on which it is mounted, such that said variable diameter extended-tip angioplasty balloon could be introduced over a guidewire into a blood vessel without the use of a vascular sheath, and the larger O.D. toward the hub end of the catheter would obturate, or prevent hemorrhage from, said arteriotomy enlarged by entry of the balloon. An extended-tip angioplasty balloon catheter with a variable diameter configuration could be used for a sheathless procedure, where, for example, needle access is achieved in a peripheral extremity artery, such as a radial artery or pedal artery, using a splittable needle such as in U.S. Pat. No. 3,382,872, a guidewire pre-loaded in an extended-tip angioplasty balloon catheter introduced into the peripheral extremity artery through said splittable needle, said needle split away, and then said extended-tip angioplasty balloon catheter advanced over the guidewire and into the peripheral extremity artery without any sheath. An extended-tip angioplasty balloon catheter with a shaped tip as a means to impart steerability and permit selective catheterization and angioplasty of potentially any artery in the body from this sheathless access using only the single catheter. Although advancement of typical angioplasty balloon catheters without sheaths can result in oversizing of the vascular access arteriotomy compared to the catheter shaft where the balloon isn't mounted, with a variable shaft extended-tip angioplasty balloon catheter the outer diameter (O.D.) of the shaft on the hub side of the balloon or on the tip side of the balloon (or both) can be made larger than the O.D. of the balloon, thereby obturating any hemorrhage at the vascular access arteriotomy site and permitting a sheathless procedure to be done. For example, and entire tibial artery angiography and angioplasty procedure is possible using this method with only a needle, guidewire, and extended-tip angioplasty balloon catheter. Other vascular territories could be similarly treated, including for example carotid arteries, iliac arteries, renal arteries, coronary arteries, or veins. Furthermore, using a peel away introducer, the method would be understood by those knowledgeable in the field as a means to perform vascular stent procedures, including arterial stent procedures for example carotid artery stent placement, renal artery stent placement, coronary artery stent placement, and venous stent placement.

An extended-tip angioplasty balloon catheter would facilitate performance of angioplasty for anastomotic stenoses of arteriovenous fistulae or grafts when the fistula or graft are the access point because the extended tip could be passed over a guidewire proximally in the inflow artery for several centimeters or more, aiding the passage of the balloon through the stenotic anastomosis. An extended-tip angioplasty balloon catheter would facilitate cornering and tracking of the angioplasty balloon catheter through tortuous blood vessels. When dilating an anastomic stenosis in an AVAC, for example, it is desirable to preserve inflow into the fistula regardless of the outcome of the angioplasty. An extended-tip angioplasty balloon catheter takes a gentle curve across the anastomosis that would reduce trauma on the anastomosis and adjacent artery and vein during balloon inflation. An extended-tip angioplasty balloon catheter also preserves access across the anastomosis and prevent kinking of the guidewire, eliminating the risk of losing guidewire access to the inflow artery. Finally, with side holes placed in an extended-tip segment of the angioplasty balloon, with retraction of said angioplasty balloon after said balloon's inflation and deflation wholly into the accessed outflow vein or graft, with enough tolerance around the guidewire, and use of a side arm (e.g., Touhy-Borst) adapter, contrast could be injected to perform post-angioplasty angiography to check the results of the angioplasty procedure without the need to remove or exchange the extended-tip angioplasty balloon catheter. Similarly, if no side holes are present on the extended-tip segment, the guidewire can be removed and contrast injected to exit the catheter tip end hole, which from its position in the supplying artery would also allow fluoroscopic or radiographic images of the anastomosis, stenosis, and juxta-anastomotic AVAC to be obtained. Finally, if a semi-compliant balloon (e.g., manufactured using polyether block amide (Pebax) or higher-durometer polyurethane) were used, the balloon inflation procedure could be done multiple times with sequentially larger balloon inflation pressures, and therefore balloon diameters, with angiography between each inflation/deflation to check results, all with a single catheter. This would be a major advance over currently available angioplasty balloons. The advantages of an extended-tip angioplasty balloon catheter for treating stenoses or hemodialysis AVAC arterial anastomoses are:

(a) Flexibility comparable to a diagnostic catheter, and would be less likely to cause trauma to a blood vessel beyond a stenosis even if said blood vessel had a substantial angle just beyond the stenosis.

(b) Improved tracking and cornering of the angioplasty balloon catheter through tortuous blood vessels.

(c) Less acute curvature during balloon inflation within a blood vessel that is curved, as a means of lowering the risk of vessel injury or rupture during balloon inflation compared with a standard tip angioplasty balloon catheter.

(d) A means of lowering the chance of kinking a guidewire when used to dilate a vessel with an acute angle just beyond the stenosis.

(e) After angioplasty, despite retraction of the balloon into the AVAC outflow, an extended-tip angioplasty balloon catheter would still retain catheter access across the treated stenosis and into the inflow artery, thereby establishing a means to perform post-angioplasty contrast injection and imaging of the angioplasty site using fluoroscopy or radiography without the need for any catheter exchanges, saving procedure time, procedure cost, equipment cost, and reducing radiation to the patient and operator. This maneuver may be aided by side holes placed in the extended-tip segment distal to the angioplasty balloon. From this position, the guidewire can be removed without any loss of access across the stenosis, anastomosis, and into the supplying artery.

(f) "Blow back" technique to image the angioplasty site after angioplasty would not be needed, reducing the risks of that technique, including vessel injury or embolization of plaque, intimal debris, or blood clot retrograde into the arterial circulation, thereby reducing ischemic complications including pain, ulceration, loss of sensation, gangrene, and amputation.

(g) If a rupture is observed after angioplasty, the same extended-tip angioplasty balloon catheter that performed the angioplasty can be manipulated across the ruptured blood vessel and inflated, thereby facilitating and expediting control of extravasation or hemorrhage compared to imaging methods that require removal of the angioplasty balloon catheter from the body, as is typically done post-angioplasty unless the "blow back" technique is used.

(h) Using an extended-tip angioplasty balloon catheter with a shape or angle at the distal tip end of the extended tip allows the catheter to be used for selective catheterization like a diagnostic catheter, potentially obviating the need for a separate diagnostic catheter either pre- or post-angioplasty. Such a shape could be for example a multi-purpose shape (e.g., "hockey stick"), a simple curve (e.g., renal guide or LIMA guide shape), or may even have more than one curve such as a visceral selective shape (e.g., "Cobra"), more complex shapes (e.g., "Mikaelson", LGA), or even a reverse curve shape (e.g, Simmons 1 or Simmons 2).

(i) Because multiple catheter exchanges are avoided with an extended-tip angioplasty balloon catheter, there is less chance of trauma at the vascular access insertion site, and less need to use vascular sheaths for access into the AVAC, especially if a variable diameter catheter is used, such that the catheter shaft O.D. proximal to the balloon is somewhat larger than the balloon O.D. when not inflated.

(j) An extended-tip angioplasty balloon catheter can have a long taper similar to a vessel dilator, as a means to facilitate the passage of an angioplasty balloon across a stenosis despite its severity, configuration, or composition.

An extended-tip angioplasty balloon catheter with side holes distal to the balloon and a segment in the tip that is shaped could be used to perform an arteriogram and angioplasty in its entirety, as described in the following steps:

(a) Obtain needle access into an outflow tract of a AVAC using Seldinger's technique or a modification thereof;
(b) Pass a guidewire through said needle;
(c) Remove said needle from the body;
(d) Introduce an extended-tip angioplasty balloon catheter over said guidewire;
(e) If the guidewire has traversed the AVAC arterial anastomosis and passed proximally into the supplying artery, advance the extended-tip angioplasty balloon catheter over said guidewire and into the supplying artery;
(f) If the guidewire has not traversed the AVAC arterial anastomosis and passed proximally into the supplying artery but remains in the AVAC outflow tract, remove the guidewire, and use the extended-tip angioplasty balloon catheter to inject contrast and examine the stenosis, anastomosis, and vascular anatomy, then use the extended-tip angioplasty balloon catheter with a shaped distal tip to selectively catheterize the supplying artery, with or without using a guidewire;
(g) Inject contrast into the extended-tip angioplasty balloon catheter and obtain fluoroscopic or radiographic images;
(h) Manipulate the extended-tip angioplasty balloon catheter over the guidewire so that the balloon is positioned centrally across the anastomotic stenosis, if present;
(i) Inflate the angioplasty balloon to the desired pressure, if using a compliant balloon adjust the pressure of the inflation to achieve the desired balloon diameter;
(j) Deflate the balloon, and retract the extended-tip angioplasty balloon catheter until the balloon is wholly within the outflow tract and not across the stenosis or in the supplying artery;
(k) Either with the guidewire in place, or with it removed, inject contrast into the appropriate lumen of the extended-tip angioplasty balloon catheter;
(l) Obtain radiographic or fluoroscopic images of the angioplasty site;
(m) If the images show that the angioplasty appears satisfactory the extended-tip angioplasty balloon catheter can be removed and hemostasis of the access site achieved;
(n) If the images show that the angioplasty appears unsatisfactory due to lack of sufficient dilation the extended-tip angioplasty balloon catheter can be advanced over the guidewire and across the stenosis, from where a repeat angioplasty can be done. If desired, a semi-compliant balloon can be inflated to higher inflation pressure, thereby achieving a larger diameter angioplasty;
(o) If the images reveal a complication is noted like a rupture, the extended-tip angioplasty balloon can be manipulated across the rupture and inflated to obturate the hemorrhage.

In this regard, there is a need for an extended-tip angioplasty balloon catheter suited to the unique anatomy of the AVAC and the tasks that are required of the angioplasty balloon catheter in this situation. By allowing a balloon angioplasty catheter to perform the functions of both a traditional diagnostic catheter as well as a traditional angioplasty balloon catheter would allow the evaluation and treatment for stenoses on the AVAC inflow to be handled in a safer, faster and easier manner. An extended-tip angioplasty catheter comprises a distal end significantly longer that the traditional 3-5 mm balloon tip, e.g., 3 cm to 75 cm. By having an extended-tip segment as the leading end, the extended-tip balloon catheter permits the balloon portion of the catheter itself to track easily across angulated or tortuous anatomy in much the same way as a standard diagnostic catheter tracks across such vascular segments. The catheter performance is enhanced by having the distal catheter portion constructed with an angled or shaped tip, facilitating selective catheterization of a vessel that projects at an angle to the long axis of the accessed venous outflow segment or graft of the AVAC.

DETAILED DESCRIPTION

Figure 1:
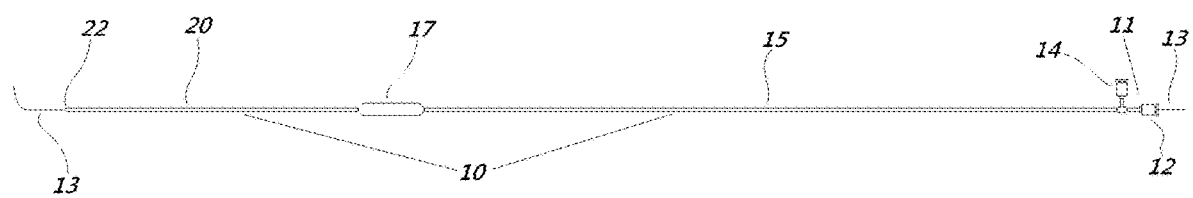
FIG. 1 shows an exemplary embodiment of the invention comprising an angioplasty balloon with extended tip, lateral view.

Referring now to FIG. 1, there is shown an examplary embodiment of the present invention that comprises an extended-tip angioplasty balloon catheter 10, wherein said extended-tip angioplasty balloon catheter 10 has at least one lumen to accommodate a guidewire 13, said guidewire port configuration comprising either an Over-the-Wire (OTW) or Rapid Exchange (Rx) design. The catheter 10 comprises a balloon 17 positioned on the shaft of the catheter, a catheter segment 15 proximal to the balloon 17, and a catheter extended-tip segment 20 distal to the balloon 17. In this example, the catheter segment proximal to the balloon also includes a hub end 11, comprising at least one hub adapter 12 for a guidewire lumen and another hub adapter 14 for inflation of the balloon 17. The catheter 10 also comprises a distal end hole 22, and in this example the catheter 10 is shown with a guidewire entering its hub end 11 through hub adapter 12 and said guidewire 13 exiting the catheter at the distal end hole 11. In this embodiment, the proximal catheter segment 15 may extend from 20 cm to 240 cm in length proximal to the balloon 17, and the distal catheter extended-tip segment 20 may extend from 3 cm to 75 cm distal to the angioplasty balloon 17.

Figure 2:
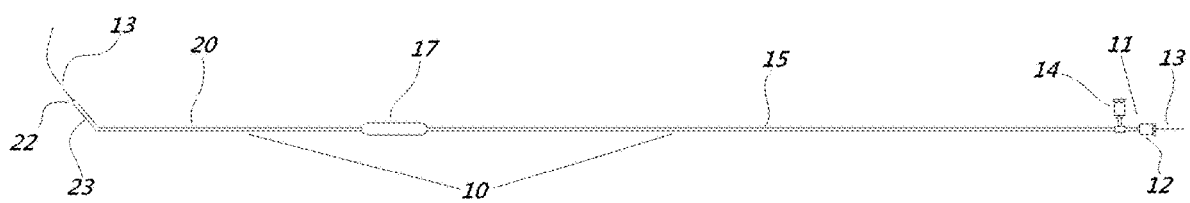
FIG. 2 illustrates an alternative embodiment of the invention comprising an angioplasty balloon with extended tip, in this example showing an angled element at the distal end of the extended tip, lateral view.

In FIG. 2 another embodiment of the invention is shown comprising an extended-tip angioplasty balloon catheter 10, in this example the catheter extended-tip segment 20 has an angled segment 23 at its distal end, such that the long axis of the angled segment 23 is not coaxial with the long-axis of the distal catheter extended-tip segment 20, but rather is off-axis by at least 5 degrees, and the angled segment 23 is at least 1 cm long and as long as 20 cm.

Figure 3:
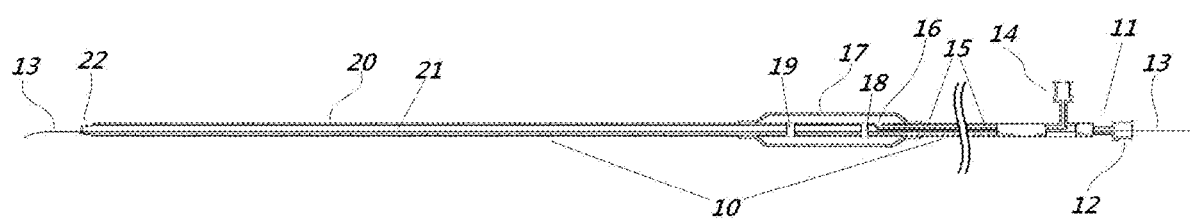
FIG. 3 a longitudinal section of an exemplary embodiment of the invention comprising an angioplasty balloon with an extended tip.

FIG. 3 is a magnified cut-away view of an embodiment of the invention that comprises an extended-tip angioplasty balloon catheter 10, wherein said extended-tip angioplasty balloon catheter 10 has at least one lumen 21 to accommodate a guidewire 13 or injection of contrast or medication (not shown), said guidewire port configuration comprising either an Over-the-Wire (OTW) or Rapid Exchange (Rx) design, and said guidewire outer diameter (O.D.) comprising a range from 0.009" to 0.038". The catheter 10 comprises an angioplasty balloon 17 positioned on a shaft of the catheter, a catheter segment 15 proximal to the balloon 17, and a catheter extended-tip segment 20 distal to the balloon 17. In this example, the catheter segment proximal to the balloon also includes a hub end 11, comprising at least one hub adapter 12 for a guidewire lumen and another hub adapter 14 for inflation of the balloon 17. The extended-tip angioplasty balloon 10 also comprises at least one other lumen 15 for injection of fluid or gas to inflate said angioplasty balloon 17, said other lumen also comprising an exit port 16 extending from the proximal catheter segment 15 into the inside of the angioplasty balloon 17. In this example, the angioplasty balloon 17 contains at least one proximal radiopaque marker band 18 and at least one distal radiopaque marker band 19 affixed to its catheter segment to permit visualization of the angioplasty balloon using fluoroscopy or radiography. The catheter 10 also comprises a distal end hole 22, and in this example the catheter 10 is shown with a guidewire entering its hub end 11 through hub adapter 12 and said guidewire 13 exiting the catheter at the distal end hole 11. In this embodiment, the proximal catheter segment 15 may extend from 20 cm to 240 cm in length proximal to the balloon 17, and the distal catheter extended-tip segment 20 may extend from 3 cm to 75 cm distal to the angioplasty balloon 17.

Figure 4:
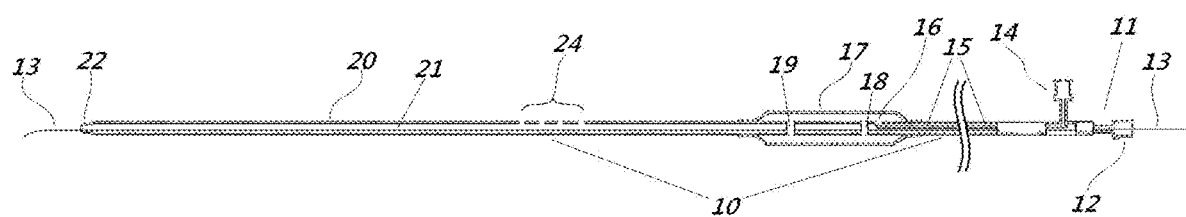
FIG. 4 is a longitudinal section of another representative embodiment of the invention comprising an angioplasty balloon with an extended tip, in this example also showing side holes in the extended tip.

Turning now to FIG. 4, an exemplary embodiment of the invention is demonstrated that illustrates an extended-tip angioplasty balloon catheter that comprises one or more side holes 24 in a distal catheter segment 20, thereby permitting injection of radiopaque contrast or medication distal to the angioplasty balloon around the guidewire 13, without needing to remove the guidewire 13.

Figure 5:
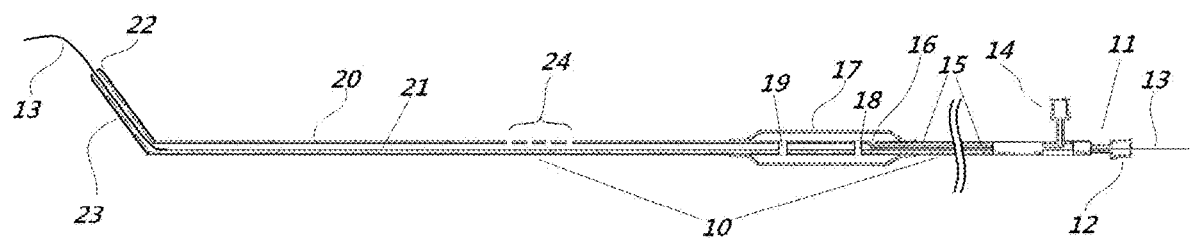
FIG. 5 is a longitudinal section view of one embodiment of the invention comprising an angioplasty balloon with an extended tip, in this example showing an angled distal tip component and side holes in the extended tip.

In FIG. 5, an embodiment of the invention is shown that comprises an extended-tip angioplasty balloon catheter 10, with an angled segment 23 at its distal end, such that the long axis of the angled segment 23 is not coaxial with the long-axis of the distal catheter extended-tip segment 20, but rather is off-axis by at least 5 degrees, and the angled segment 23 is at least 1 cm long and as long as 20 cm.

Figure 6:
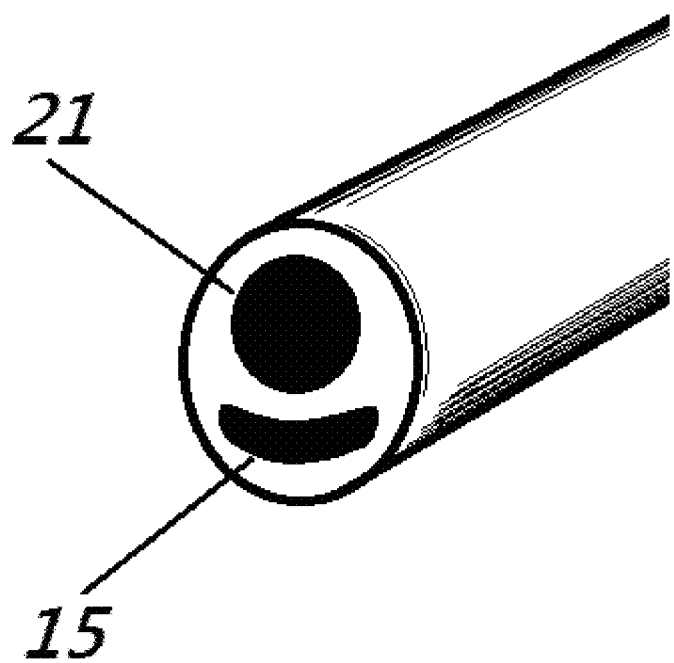
FIG. 6 is a view of an oblique cross-section of an example of the invention comprising a dual-lumen catheter, with parallel lumens.

FIG. 6 is a view of an exemplary embodiment of the invention, showing the proximal catheter segment in oblique cross-section, and at least one first lumen 21 for slidable passage of a guidewire (not shown) there through, and at least one second lumen 15 that is not coaxial with the first lumen 21, used for injection of fluid or gas to inflate the angioplasty balloon (not shown).

Figure 7:
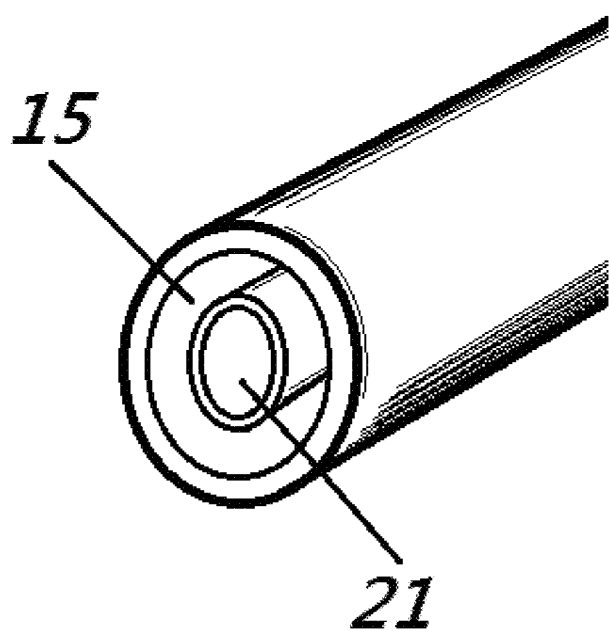
FIG. 7 is a view of an oblique cross-section of an example invention comprising a dual-lumen catheter, with coaxial lumens.

FIG. 7 is a view of an exemplary embodiment of the invention, showing the proximal catheter segment in oblique cross-section, and at least one first lumen 21 for slidable passage of a guidewire (not shown) there through, and at least one second lumen 15 that is coaxial with the first lumen 41, used for injection of fluid or gas to inflate the angioplasty balloon (not shown).

Figure 8:
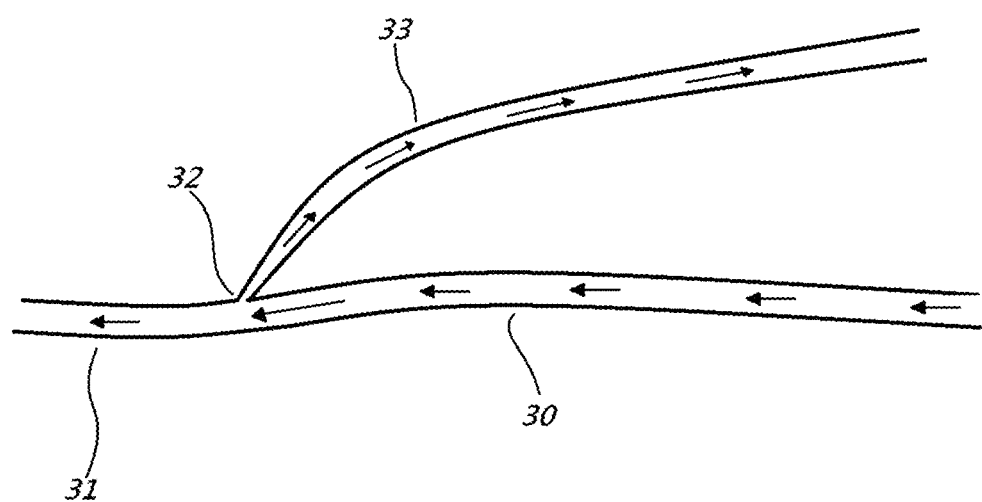
FIG. 8 is a schematic of an example of an arterial-venous fistula, lateral view.

FIG. 8 is a schematic representation of an exemplary arteriovenous circuit, lateral view, such as can be created surgically to accommodate hemodialysis, comprising an inflow artery 30, and outflow artery 31, an artero-venous anastomosis 32, and an outflow vein 33. Arrows demonstrate for illustration purposes the direction of blood flow within this exemplary arteriovenous circuit.

Figure 9:
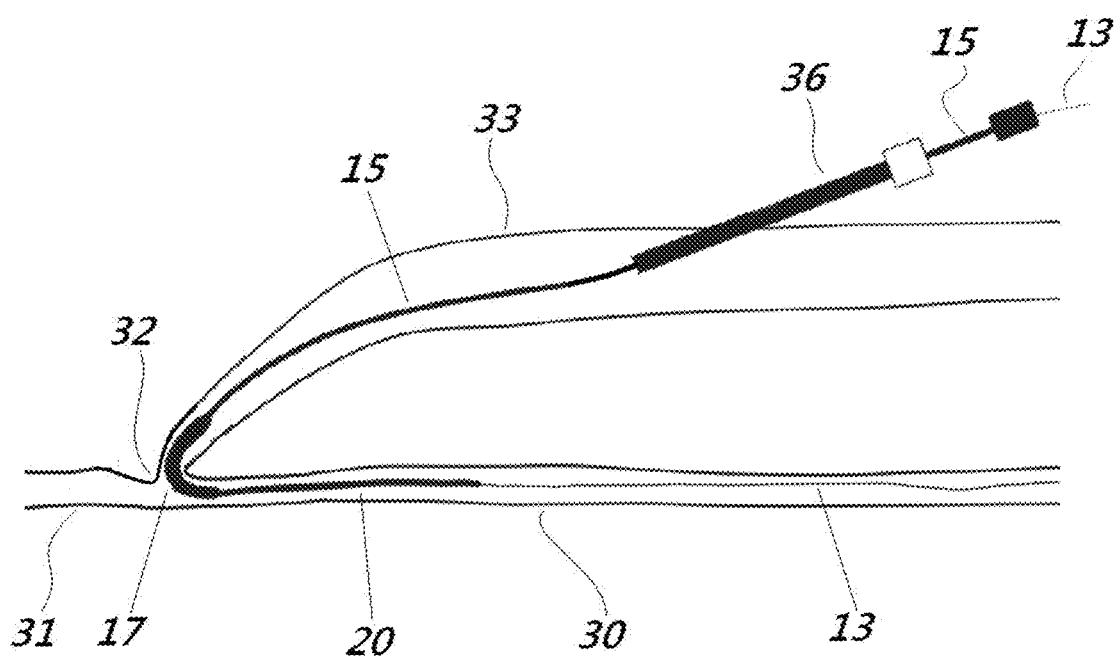
FIG. 9 is an illustration of an embodiment of the extended-tip angioplasty method, lateral view.

FIG. 9 is a schematic representation of an exemplary arteriovenous arterial circuit, comprising an inflow artery 30, an outflow artery 31, an outflow vein 33, and an arteriovenous anastomosis 32, in this example the arteriovenous anastomosis 32 is stenotic. An extended-tip angioplasty balloon catheter 10 with a proximal segment 15 and a distal extended-tip segment 20 has been introduced through the skin in this example through a vascular sheath 36 over a guidewire 13, with an angioplasty balloon 17 positioned across the arteriovenous anastomosis 32 in position to dilate said stenosis upon balloon 17 inflation. After inflation, the extended-tip angioplasty balloon catheter can be retracted so that the balloon 17 is wholly within the venous outflow segment and not across said stenosis at the anastomosis 32, and contrast injected into the extended-tip angioplasty balloon catheter hub (not shown) will exit the guidewire lumen 21 at the side holes 24, thereby opacifying the segment of interest where the angioplasty was performed without the need to remove said extended-tip angioplasty balloon catheter 10 from the body.

Figure 10:
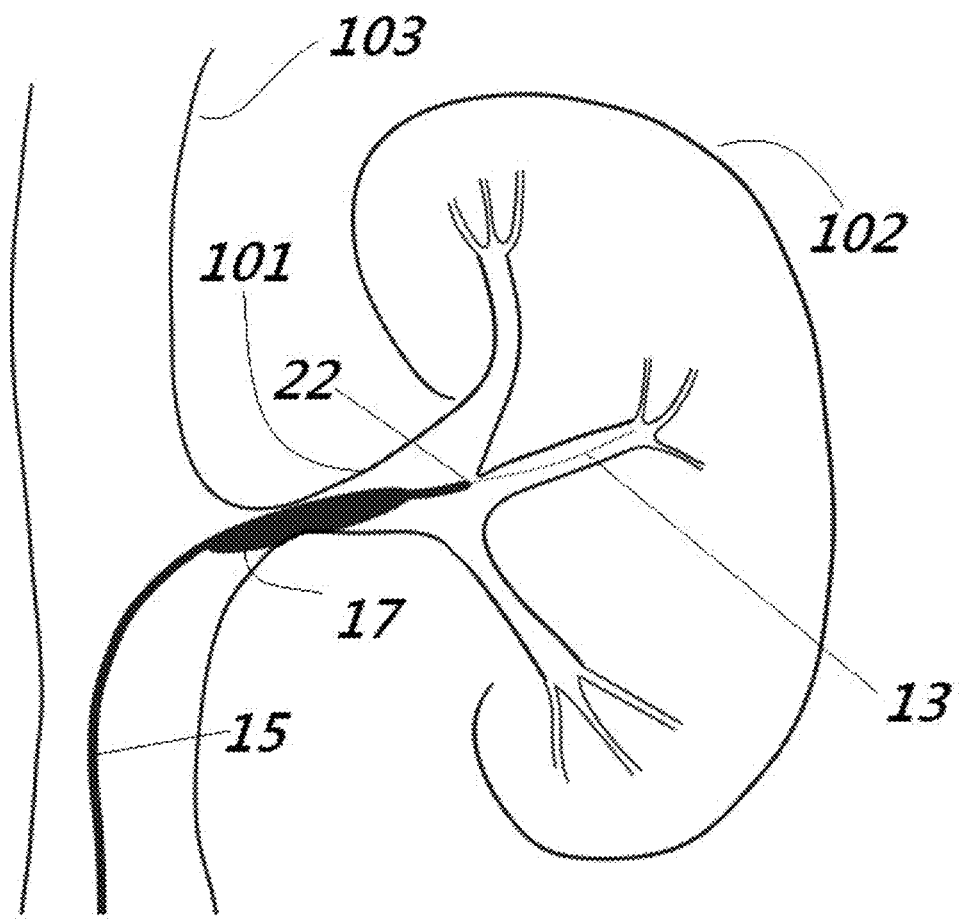
FIG. 10 is an illustration of an embodiment of an angioplasty procedure in an artery, in this example the renal artery.

FIG. 10 is a schematic illustration of a typical angioplasty of an artery, in this case a renal artery 101, using a conventional angioplasty balloon. In this example, it can be seen that there is a guidewire 13 over which the conventional angioplasty balloon catheter has been introduced, but in this case the catheter consists of a proximal shaft 15 and balloon 17, but the distal extended tip is not present in this example, and the catheter ends at its end hole 22 within substantially 5 mm of the distal end of said balloon. Also shown is an aorta 103 and a kidney 102. It can be appreciated by those familiar with the field that said angioplasty balloon 17 could have a stent mounted there to for delivery into the artery. Similarly, said angioplasty balloon 17 could have a coating including antiproliferative medication for delivery into said artery, or have affixed longitudinally a plurality of shallow cutting blades. It can also be envisioned by those familiar with the field that the angioplasty balloon catheter could be introduced into the body using a pedal artery access, or a radial artery access, in which latter case the angioplasty balloon catheter would enter the field from above.

INCORPORATION BY REFERENCE

References and citations to other documents, such as patents, patent applications, provisional patent applications, patent publications, journals, books, papers, web content, that have been made throughout this disclosure are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

CONCLUSIONS

The reader will see that an extended-tip angioplasty balloon catheter of the various embodiments described herein offers numerous advantages, particularly when used for angioplasty in tortuous blood vessels, or as a stand-alone catheter used by itself for an entire diagnostic angiogram and angioplasty, without the need for any other catheter, and even in some embodiments without the need for any vascular access sheath. Additionally, an extended-tip imparts the feature of steerability in some embodiments, thereby enabling selective catheterization, and also reduces the angle when used to dilate vessels that are not straight but rather have acute angles, thereby reducing trauma, the risk of guidewire kinking, and the chance of vessel injury.

The foregoing descriptions of specific embodiments of the present invention have been presented for purposes of illustration and description. They are not intended to be exhaustive or to limit the present invention to the precise forms disclosed, and obviously many modifications and variations are possible in light of the above teaching. The exemplary embodiment was chosen and described in order to best explain the principles of the present invention and its practical application, to thereby enable others skilled in the art to best utilize the present invention and various embodiments with various modifications as are suited to the particular use contemplated.

What is claimed is:

1. In combination, a medical angioplasty balloon catheter for use in angioplasty procedures comprising:
    (a) a catheter having a hub end and a tip end,
    (b) said catheter comprising a plurality of lumens, said plurality of lumens comprising at least a first lumen which is a means for passage of a guide wire or injection of fluids therethrough, said first lumen substantially circumscribed by a cylindrical hollow tube with imperforate walls extending from said hub end to said tip end as a means for containing fluid within said first lumen between said hub end and said tip end, said plurality of lumens also comprising at least a second lumen as a means for inflation of an expansile balloon,
    (c) said expansile balloon securely mounted on said catheter, disposed toward said tip end of said catheter,
    (d) said catheter including a first segment distal to said expansile balloon and a second segment including and proximal to said expansile balloon,
    (e) said first segment having a predetermined length of at least 2 cm.

2. In combination, a method of performing an angioplasty of a blood vessel comprising:
    (a) using an angioplasty balloon catheter having a hub end and a tip end, also comprising a plurality of lumens, said angioplasty balloon catheter further comprising an expansile balloon mounted on said catheter biased toward the tip end of said catheter, wherein said plurality of lumens comprise at least a first lumen which is a means for passage of a guide wire or injection of fluids therethrough, said first lumen substantially circumscribed by a cylindrical hollow tube with imperforate walls extending from said hub end to said tip end as a means for containing fluid within said first lumen between said hub end and said tip end, said plurality of lumens also comprising at least a second lumen as a means for inflation of the expansile balloon, said angioplasty balloon catheter further comprising a first segment distal to said expansile balloon and a second segment including and proximal to said expansile balloon, said first segment having a predetermined length of at least 2 cm,
    (b) manipulating said angioplasty balloon catheter so that the first segment traverses a stenosis within a blood vessel, (c) further manipulating said angioplasty balloon catheter to position said expansile balloon substantially central within said stenosis,
(d) inflating said expansile balloon,
(e) deflating said expansile balloon,
(f) manipulating said angioplasty balloon substantially out of said stenosis.

3. In combination, a medical angioplasty balloon catheter for use in angioplasty procedures comprising:
(a) a catheter having a hub end and a tip end,
(b) said catheter comprising a plurality of lumens, said plurality of lumens comprising at least a first lumen which is a means for passage of a guide wire or injection of fluids therethrough, said first lumen substantially circumscribed by a cylindrical hollow tube extending from said hub end to said tip end, said plurality of lumens also comprising at least a second lumen as a means for inflation of an expansile balloon,
(c) said expansile balloon securely mounted on said catheter, disposed toward said tip end of said catheter,
(d) said catheter including a first segment distal to said expansile balloon and a second segment including and proximal to said expansile balloon, wherein a sidewall of the first lumen is imperforate throughout the second segment,
(e) said cylindrical hollow tube of said first lumen further comprising at least a perforation within 75 cm distal to said expansile balloon as a means for exit of fluids injected therethrough,
(f) said first segment having a predetermined length of at least 2 cm.

4. In combination, a medical angioplasty balloon catheter for use in angioplasty procedures comprising:
(a) a catheter having a hub end and a tip end,
(b) said catheter comprising a plurality of lumens, said plurality of lumens comprising at least a first lumen which is a means for passage of a guide wire or injection of fluids therethrough, said first lumen substantially circumscribed by a cylindrical hollow tube extending from said hub end to said tip end, said plurality of lumens also comprising at least a second lumen as a means for inflation of an expansile balloon,
(c) said expansile balloon securely mounted on said catheter, disposed toward said tip end of said catheter,
(d) said catheter comprising a first segment distal to said expansile balloon, wherein a sidewall of the first lumen is imperforate throughout the first segment, and a second segment including and proximal to said expansile balloon,
(e) said second segment further comprising at least a perforation in said first lumen within 75 cm proximal to said expansile balloon as a means for exit of fluids injected therethrough,
(f) said first segment having a predetermined length of at least 2 cm.

5. In combination, a method of performing an angioplasty of a blood vessel comprising:
(a) using an angioplasty balloon catheter having a hub end and a tip end, also comprising a plurality of lumens, said angioplasty balloon catheter further comprising an expansile balloon mounted on said catheter biased toward the tip end of said catheter; wherein said plurality of lumens comprise at least a first lumen which is a means for passage of a guide wire or injection of fluids therethrough, said plurality of lumens also comprising at least a second lumen as a means for inflation of the expansile balloon; said angioplasty balloon catheter further comprising a first segment distal to said expansile balloon and a second segment including and proximal to said expansile balloon, wherein a sidewall of the first lumen is imperforate throughout the second segment, said first segment having a predetermined length of at least 2 cm, said first lumen further comprising at least a perforation in said first segment within 75 cm distal to said expansile balloon as a means for exit of fluids injected therethrough,
(b) manipulating said angioplasty balloon catheter so that the first segment traverses a stenosis within a blood vessel,
(c) further manipulating said angioplasty balloon catheter to position said expansile balloon substantially central within said stenosis,
(d) inflating said expansile balloon,
(e) deflating said expansile balloon,
(f) manipulating said angioplasty balloon substantially out of said stenosis.

6. In combination, a method of performing an angioplasty of a blood vessel comprising:
(a) using an angioplasty balloon catheter having a hub end and a tip end, also comprising a plurality of lumens, said angioplasty balloon catheter further comprising an expansile balloon mounted on said catheter biased toward the tip end of said catheter; wherein said plurality of lumens comprise at least a first lumen which is a means for passage of a guide wire or injection of fluids therethrough, said plurality of lumens also comprising at least a second lumen as a means for inflation of the expansile balloon; said angioplasty balloon catheter further comprising a first segment distal to said expansile balloon, wherein a sidewall of the first lumen is imperforate throughout the first segment, and a second segment including and proximal to said expansile balloon, said first segment having a predetermined length of at least 2 cm, said second segment further comprising at least a perforation in said first lumen within 75 cm proximal to said expansile balloon as a means for exit of fluids injected therethrough,
(b) manipulating said angioplasty balloon catheter so that the first segment traverses a stenosis within a blood vessel,
(c) further manipulating said angioplasty balloon catheter to position said expansile balloon substantially central within said stenosis,
(d) inflating said expansile balloon,
(e) deflating said expansile balloon,
(f) manipulating said angioplasty balloon substantially out of said stenosis.

7. The medical angioplasty balloon catheter of any one of claims 1, 3 or 4, wherein the predetermined length of the first segment is substantially between 2 cm and 75 cm.

8. The medical angioplasty balloon catheter of any one of claim 1, 3 or 4, wherein the predetermined length of the first segment is substantially between 5 cm and 75 cm.

9. The medical angioplasty balloon catheter of any one of claims 1, 3, or 4, wherein the predetermined length of the first segment is configured to facilitate performance of an angioplasty of an arteriovenous anastomosis.

10. The medical angioplasty balloon catheter of claim 3, wherein the predetermined length of the first segment is substantially between 10 cm and 75 cm.

11. The method of performing an angioplasty of a blood vessel of any of claims 2, 5, 6, wherein the predetermined length of the first segment is substantially between 2 cm and 75 cm.

12. The method of performing an angioplasty of a blood vessel of any of claims 2, 5, 6, wherein the predetermined length of the first segment substantially between 5 cm and 75 cm.

13. The method of performing an angioplasty of any one of claims 2, 5, 5, wherein the predetermined length of the first segment is configured to facilitate performance of an angioplasty of an arteriovenous anastomosis.

14. The method of performing the angioplasty of any of claims 2, 5, 6, further comprising manipulating said angioplasty balloon catheter so that said first segment traverses an acute angle within the blood vessel.

15. The method of performing an angioplasty of a blood vessel of any of claims 2, 5, 6, wherein said blood vessel is selected from the group consisting of an artery, a vein, an arteriovenous fistula, an arteriovenous graft, or an arteriovenous anastomosis.

16. The method of claim 5, wherein the predetermined length of the first segment is substantially between 10 cm and 75 cm.

\* \* \* \* \*